United States Patent
Kim

(10) Patent No.: US 12,220,275 B2
(45) Date of Patent: Feb. 11, 2025

(54) SYSTEM AND METHODS FOR INTERVENTIONAL ULTRASOUND IMAGING

(71) Applicant: GE Precision Healthcare LLC, Milwaukee, WI (US)

(72) Inventor: Jeong Seok Kim, Seongnam-si (KR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 915 days.

(21) Appl. No.: 16/573,908

(22) Filed: Sep. 17, 2019

(65) Prior Publication Data
US 2021/0077060 A1 Mar. 18, 2021

(51) Int. Cl.
| | |
|---|---|
| *A61B 8/08* | (2006.01) |
| *A61B 8/00* | (2006.01) |
| *G06N 3/08* | (2023.01) |
| *A61B 8/14* | (2006.01) |
| *A61B 10/02* | (2006.01) |
| *G06N 20/00* | (2019.01) |

(52) U.S. Cl.
CPC ............ *A61B 8/0841* (2013.01); *A61B 8/085* (2013.01); *A61B 8/5246* (2013.01); *G06N 3/08* (2013.01); *A61B 8/14* (2013.01); *A61B 8/4444* (2013.01); *A61B 8/5207* (2013.01); *A61B 10/0233* (2013.01); *G06N 20/00* (2019.01)

(58) Field of Classification Search
CPC ..... A61B 8/0841; A61B 8/085; A61B 8/5246; A61B 8/14; A61B 8/4444; A61B 8/5207; A61B 10/0233; G06N 3/08; G06N 20/00
See application file for complete search history.

(56) References Cited

U.S. PATENT DOCUMENTS

| | | | |
|---|---|---|---|
| 9,375,195 B2 | 6/2016 | Kamen et al. | |
| 9,642,592 B2 | 5/2017 | Wang et al. | |
| 2016/0058425 A1 | 3/2016 | Wong et al. | |
| 2016/0317118 A1 | 11/2016 | Parthasarathy et al. | |
| 2017/0372193 A1* | 12/2017 | Mailhe | G06T 5/005 |
| 2018/0240235 A1* | 8/2018 | Mazo | G06N 3/04 |

(Continued)

OTHER PUBLICATIONS

Mahapatra, D. et al., "Progressive Generative Adversarial Networks for Medical Image Super resolution," Cornell University arXiv Website, Available Online at https://arxiv.org/abs/1902.02144, Available as Early as Feb. 6, 2019, 21 pages.

(Continued)

*Primary Examiner* — Amal Aly Farag
(74) *Attorney, Agent, or Firm* — McCoy Russell LLP

(57) ABSTRACT

Methods and systems are provided for interventional ultrasound imaging. In one embodiment, a method comprises acquiring an ultrasound image of an anatomical region, segmenting an interventional device from the ultrasound image to obtain a segmented image, restoring an image quality of the ultrasound image to a reference image quality to obtain a restored ultrasound image, combining the segmented image with the restored ultrasound image to obtain a corrected ultrasound image, and displaying the corrected ultrasound image. In this way, ultrasound imaging may be used to image the position of an interventional device such as biopsy needle in an anatomical region, in real-time, with reduced image artifacts caused by the interventional device.

14 Claims, 6 Drawing Sheets

(56) References Cited

U.S. PATENT DOCUMENTS

| | | | |
|---|---|---|---|
| 2019/0261945 A1* | 8/2019 | Funka-Lea | A61B 8/12 |
| 2020/0334871 A1* | 10/2020 | Su | G06T 11/008 |
| 2021/0059758 A1* | 3/2021 | Avendi | A61B 8/465 |
| 2021/0321978 A1* | 10/2021 | Nguyen | G06N 3/0454 |

OTHER PUBLICATIONS

Mehrtash, A. et al., "Automatic Needle Segmentation and Localization in MRI with 3D Convolutional Neural Networks: Application to MRI-targeted Prostate Biopsy," IEEE Transactions on Medical Imaging, vol. 38, No. 4, Apr. 2019, Available Online Oct. 18, 2018, 32 pages.

* cited by examiner

SYSTEM AND METHODS FOR INTERVENTIONAL ULTRASOUND IMAGING

TECHNICAL FIELD

Embodiments of the subject matter disclosed herein relate to ultrasound imaging, and more particularly, to improving image quality for interventional ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be displayed on a display device in real time or near real time, which may assist a clinician performing a medical procedure on the patient.

SUMMARY

In one embodiment, a method comprises acquiring an ultrasound image of an anatomical region, segmenting an interventional device from the ultrasound image to obtain a segmented image, restoring an image quality of the ultrasound image to a reference image quality to obtain a restored ultrasound image, combining the segmented image with the restored ultrasound image to obtain a corrected ultrasound image, and displaying the corrected ultrasound image. In this way, ultrasound imaging may be used to image the position of an interventional device such as biopsy needle in an anatomical region, in real-time, with reduced image artifacts caused by the interventional device.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

The following description relates to various embodiments for reducing image artifacts in ultrasound images during an interventional operation. Ultrasound imaging may be used to assist in various medical procedures, such as needle biopsy, where a biopsy needle is inserted into a patient to obtain a sample of cells, or needle insertion during delivery of anesthesia, where a needle may be inserted into the fascia of a patient surrounding a nerve where anesthetic material will be administered. A clinician such as a physician or an anesthesiologist may rely on the images obtained by the ultrasound imaging system to determine where to insert the needle, for example. Missing the correct location can result in the acquisition of a biopsy from an incorrect area, or a slow or failed anesthesia for examples wherein anesthesia is delivered via needle. Often, the view interpretation (e.g., identification of the visible organs) of the ultrasound images is a visually intensive process for the clinician involving nuanced analyses such as which groups of otherwise similar textures move together. Further, the interventional device, such as the biopsy needle or anesthesia needle as illustrative examples, are typically rather small and difficult to view within the ultrasound images. Further, the quality of the ultrasound images may be degraded due to a number of image artifacts caused by the presence of the interventional device, including but not limited to reverberation, comet tail, side-lobe, beam-width, and bayonet artifacts.

Thus, according to embodiments disclosed herein, multiple types of deep learning models may be used to improve the degraded ultrasound image in real-time during the interventional session. In particular, the image artifacts caused by the interventional device are removed from ultrasound images while the image of the interventional device and the surrounding tissue are maintained, thereby improving the ability of the user to visualize the position of the interventional device with respect to the surrounding tissue.

Figure 1:
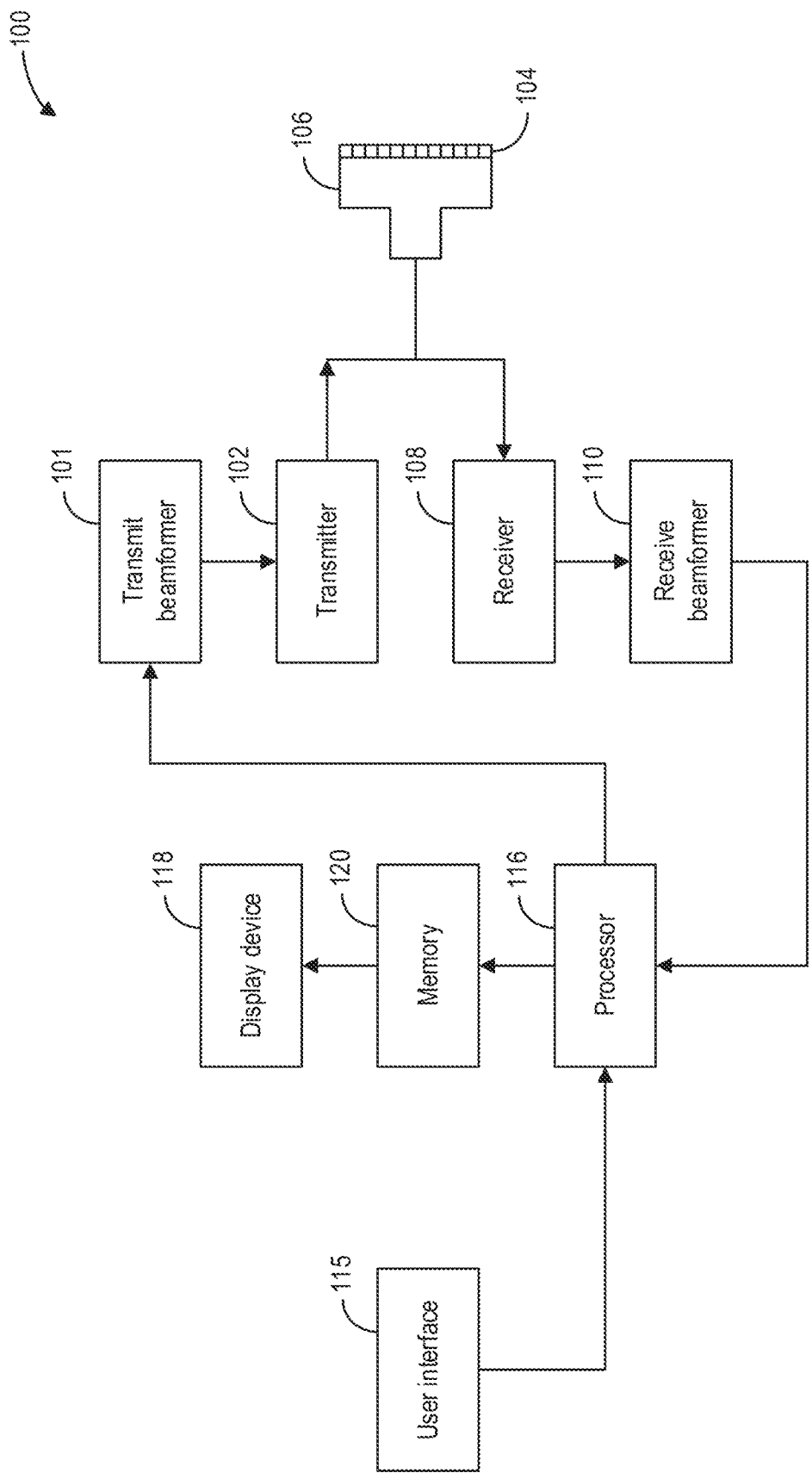
FIG. 1 shows a block diagram of an exemplary embodiment of an ultrasound system.
Figure 2:
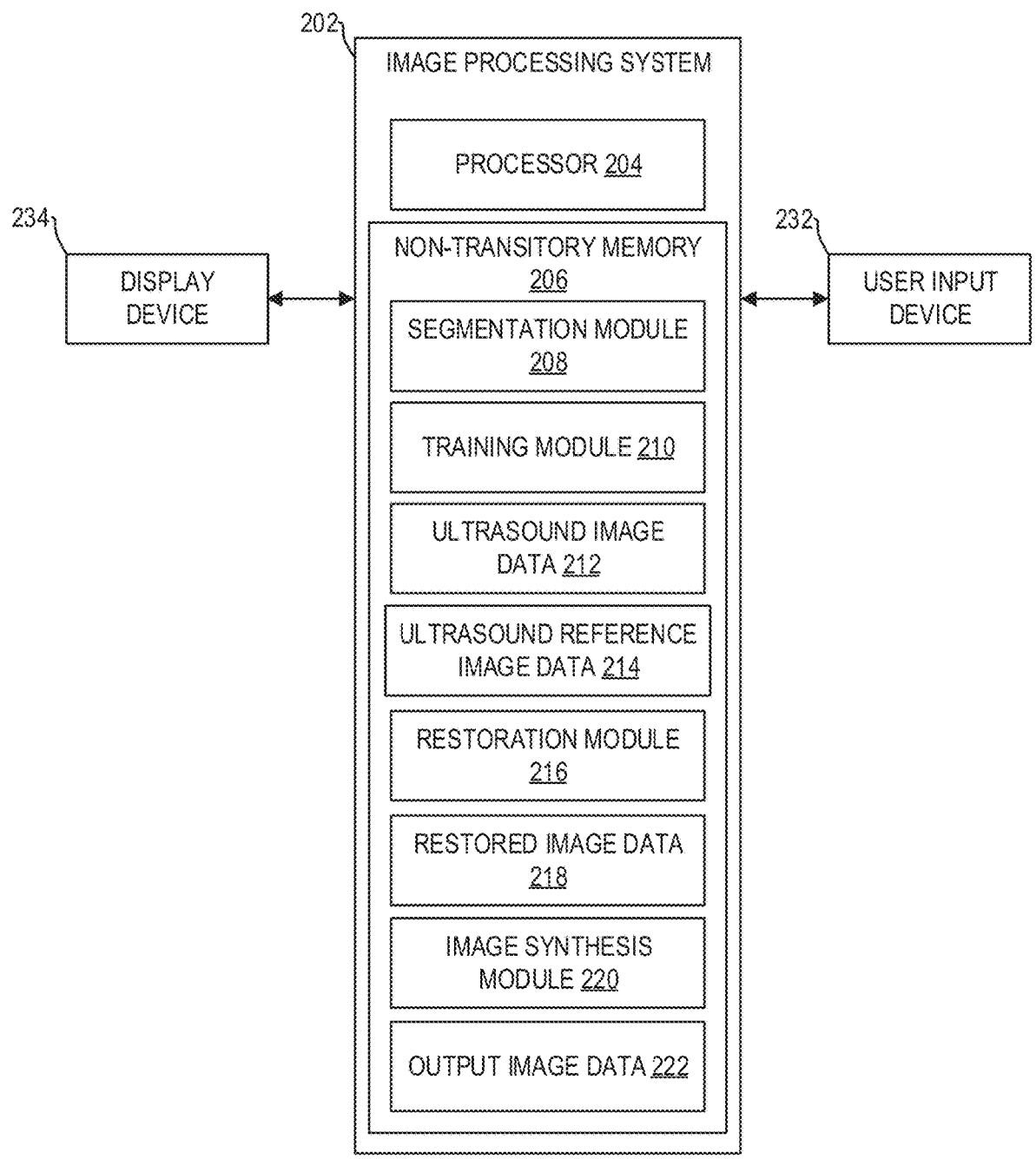
FIG. 2 is a schematic diagram illustrating a system for generating improved images, according to an exemplary embodiment.

An example ultrasound system including an ultrasound probe, a display device, and an imaging processing system are shown in FIG. 1. Via the ultrasound probe, ultrasound images may be acquired and displayed on the display device. The displayed images may have reduced image artifacts relative to the ultrasound images originally acquired via the ultrasound probe. To reduce or remove the image artifacts, an image processing system, as shown in FIG. 2, includes a segmentation module, a restoration module, and an image synthesis module. In some examples, the segmentation module may comprise a convolution neural network (CNN), such as the CNN shown in FIG. 3, for segmenting the interventional device in the acquired ultrasound images. The restoration module may comprise a generative adversarial network (GAN), such as the GAN shown in FIG. 4, for restoring the image quality of the acquired ultrasound images to the image quality of reference ultrasound images acquired prior to inserting the interventional device into the patient. The segmented images and restored images may be synthesized, as shown in FIG. 5, to create output images that do not include the image artifacts present in the original acquired ultrasound images. By configuring the segmentation module and the restoration module as described herein, image artifacts caused by an interventional device may be removed effectively in real-time during an ultrasound scan. Therefore, a method for interventional ultrasound imaging, such as the method shown in FIG. 6, includes performing the real-time processing of acquired ultrasound image data with the segmentation module and the restoration module during the interventional ultrasound scan, so that the physician may visualize the position of the interventional device relative to tissue without image artifacts.

Referring to FIG. 1, a schematic diagram of an ultrasound imaging system 100 in accordance with an embodiment of the invention is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat". In addition, the image processing system may further process the ultrasound images with a different machine learning model, such as a generative adversarial network (GAN), configured to receive the ultrasound images and reference ultrasound images as input, and output the ultrasound images with an improved image quality in accordance with the reference ultrasound images.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store segmentation module 208, training module 210, ultrasound image data 212, ultrasound reference image data 214, restoration module 216, restored image data 218, image synthesis module 220, and output image data 222. Segmentation module 208 may include one or more machine learning models, such as deep learning networks, comprising a plurality of weights and biases, activation functions, loss functions, gradient descent algorithms, and instructions for implementing the one or more deep neural networks to process input ultrasound images. For example, segmentation module 208 may store instructions for implementing a neural network, such as the convolutional neural network (CNN) 300, shown in FIG. 3. Segmentation module 208 may include trained and/or untrained neural networks and may further include training routines, or parameters (e.g., weights and biases), associated with one or more neural network models stored therein.

Non-transitory memory 206 may further include training module 210, which comprises instructions for training one or more of the machine learning models stored in segmentation module 208. In some embodiments, the training module 210 is not disposed at the image processing system 202. The segmentation module 208 thus includes trained and validated network(s).

Non-transitory memory 206 may further store ultrasound image data 212, such as ultrasound images captured by the ultrasound imaging system 100 of FIG. 1. The ultrasound image data 212 may comprise original ultrasound image data as originally acquired by the ultrasound imaging system 100, for example. The ultrasound images of the ultrasound image data 212 may therefore comprise corrupted ultrasound images, as described further herein, that include one or more image artifacts caused by the presence of an interventional device, such as a biopsy needle, in the anatomical region being imaged by the ultrasound imaging system 100. Further, ultrasound image data 212 may store ultrasound images, ground truth output, iterations of machine learning model output, and other types of ultrasound image data. In some embodiments, ultrasound image data 212 may store ultrasound images and ground truth output in an ordered format, such that each ultrasound image is associated with one or more corresponding ground truth outputs.

Non-transitory memory 206 may further store ultrasound reference image data 214, such as ultrasound reference images acquired by the ultrasound imaging system 100 of FIG. 1. The ultrasound reference images stored as ultrasound reference image data 214 comprise ultrasound images of the anatomical region acquired by the ultrasound imaging system 100 prior to insertion of the interventional device. As the reference ultrasound images are acquired without the interventional device positioned in the anatomical region, the reference ultrasound images do not include image artifacts caused by the interventional device and therefore exhibit higher image quality compared to the ultrasound images of the ultrasound image data 212.

Figure 4:
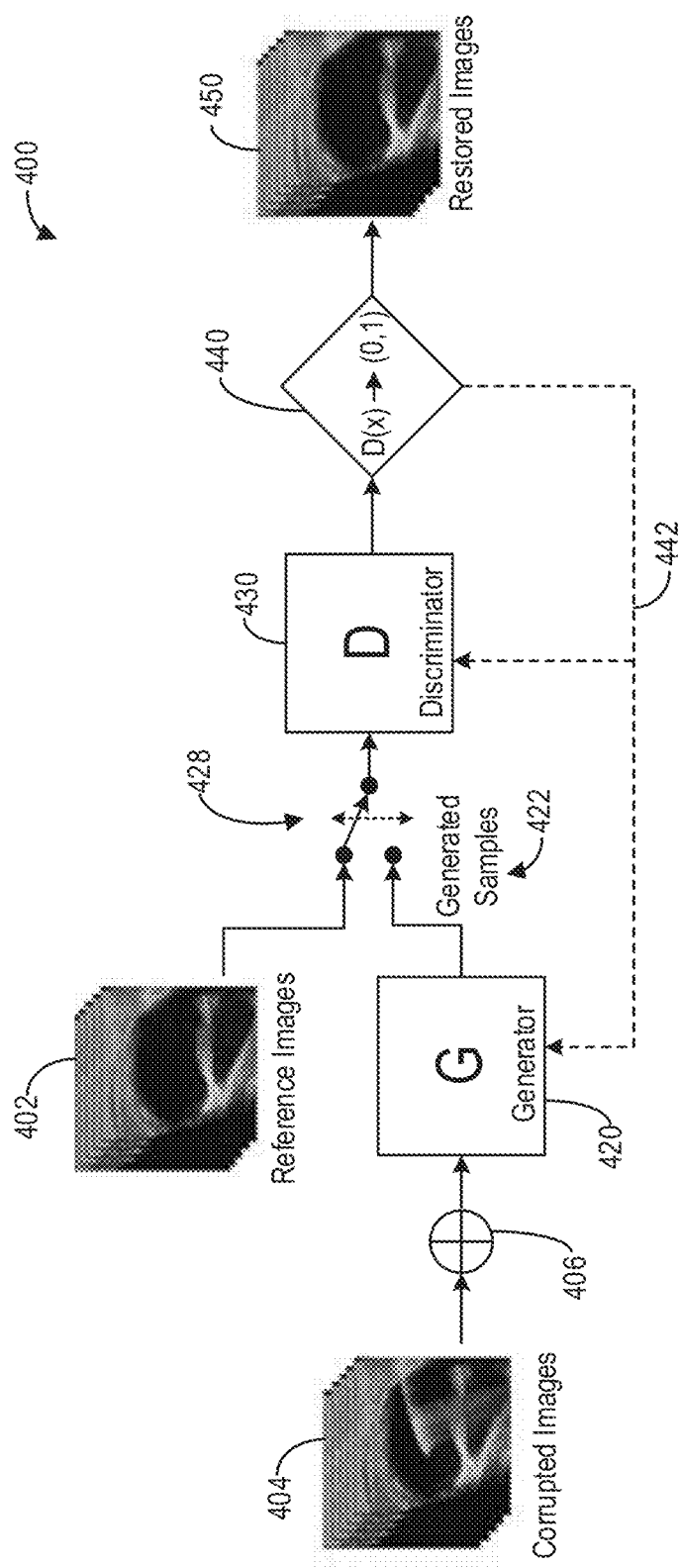
FIG. 4 is a schematic diagram illustrating an architecture of a generative adversarial network which can be used in the system of FIGS. 1 and 2, according to an exemplary embodiment.
Figure 5:
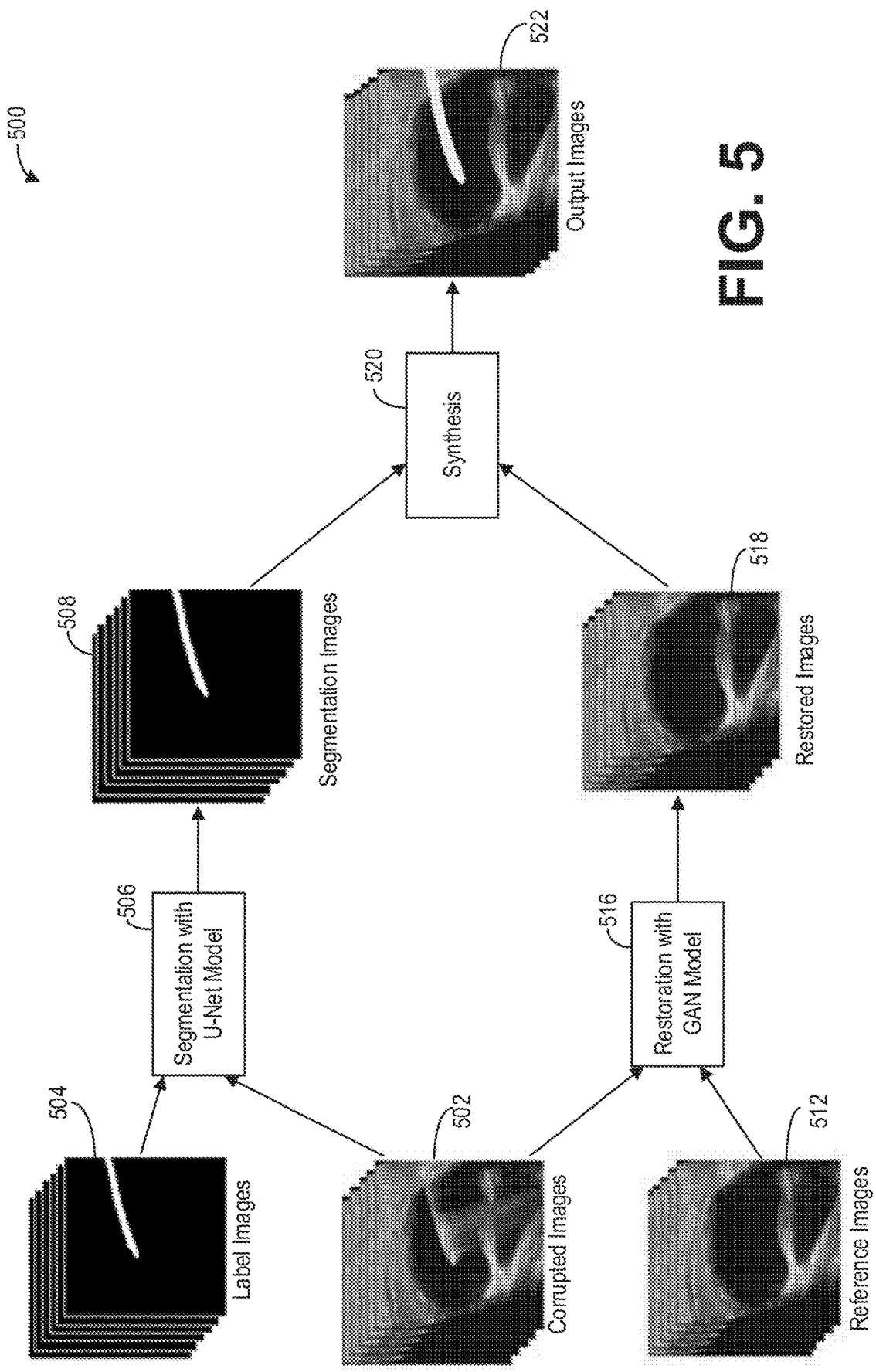
FIG. 5 is a diagram illustrating an example method for improving image quality for ultrasound images of interventional devices, according to an exemplary embodiment.

Non-transitory memory 206 may further include restoration module 216, which comprises instructions for implementing one or more neural networks configured as a generative adversarial network (GAN), such as the GAN 400 shown in FIG. 4. The restoration module 216 restores the image quality of the ultrasound image data 212 to the image quality of the ultrasound reference image data 214, as described further herein.

Non-transitory memory 206 may further include restored image data 218 generated by the restoration module 216. The restored image data 218 comprises the ultrasound image data 212 with the one or more image artifacts caused by the interventional device removed. Further, as the restoration module 216 may also remove the interventional device from the ultrasound image data 212 to create the restored image data 218, non-transitory memory 206 may further include image synthesis module 220 comprising instructions for combining the restored image data 218 with segmented images of the interventional device produced by the segmentation module 208. The image synthesis module 220 outputs the combined image data as the output image data 222 stored in the non-transitory memory 206. The output image data 222 comprises ultrasound image data corresponding to the ultrasound image data 212 with the image artifacts caused by the interventional device removed from the image data. Further, as the image synthesis module 220 combines the segmentation images from the segmentation module 208 into the restored image data 218 to create the output image data 222, the output image data 222 includes the image of the interventional device. In this way, the output image data 222 may be displayed via the display device 234 to the user, so that the user may adjust the positioning of the interventional device within the subject based on the display of the output image data 222.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an interventional device in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
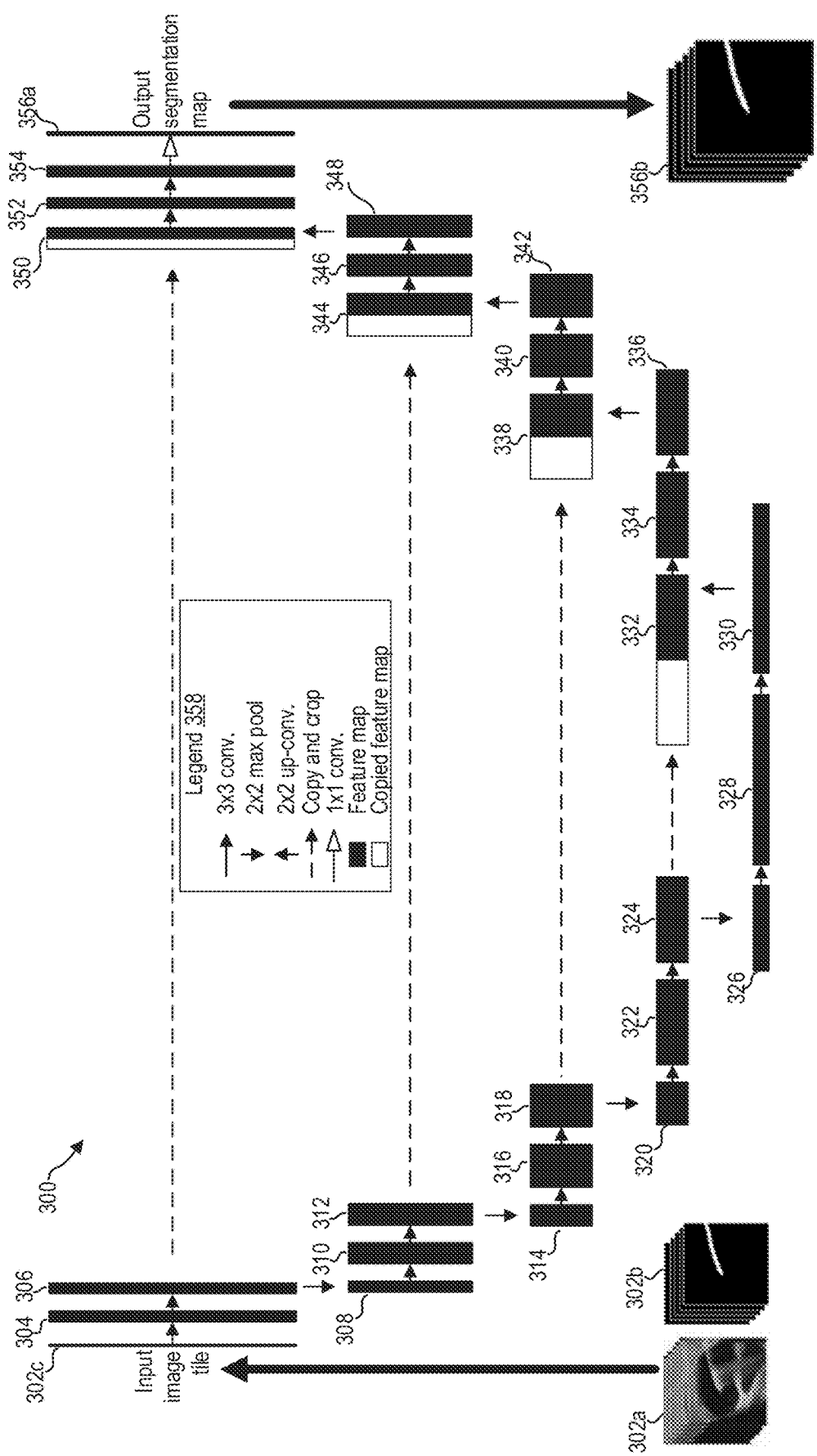
FIG. 3 is a schematic diagram illustrating an architecture of a deep neural network which can be used in the systems of FIGS. 1 and 2, according to an exemplary embodiment.

Turning to FIG. 3, CNN architecture 300 for mapping a corrupted medical image containing an interventional device to a segmented medical image of the interventional device is shown. CNN architecture 300 provides a more detailed illustration of a deep neural network, such as segmentation module 208, which may execute segmentation of an interventional device in a corrupted medical image.

CNN architecture 300 represents a U-net architecture, which may be divided into an autoencoder portion (descending portion, elements 302*b*-330) and an autodecoder portion (ascending portion, elements 332-356a). CNN architecture 300 is configured to receive medical images including one or more image artifacts as well as an image of an interventional device such as a biopsy needle, which may comprise a magnetic resonance (MR) image, computed tomography (CT) image, positron emission tomography (PET) image, X-ray image, or ultrasound image. In one embodiment, CNN architecture 300 is configured to receive data from a corrupted medical image of an anatomical region, such as corrupted medical image 302a, comprising a plurality of pixels/voxels, and map the input blurred medical image data to a segmented medical image of the same anatomical region, such as segmented medical image 356b, based on output of a segmentation map. CNN architecture 300 comprises a series of mappings, from an input image tile 302c, which may be received by an input layer, through a plurality of feature maps, and finally to an output segmented medical image 356b, which may be produced based on output from output layer 356a. In some embodiments, CNN architecture 300 is configured to receive a labeled image 302b corresponding to a labeling of the interventional device within the corrupted medical image 302a.

The various elements comprising CNN architecture 300 are labeled in legend 358. As indicated by legend 358, CNN architecture 300 includes a plurality of feature maps (and/or copied feature maps) connected by one or more operations (indicated by arrows). The arrows/operations receive input from either an external file, or a previous feature map, and transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated/mapped to a subset, or all, of the neurons in a next layer/feature map.

Feature maps may be described using the terms length, width, and depth, wherein each term refers to a number of neurons comprising the feature map (e.g., how many neurons long, how many neurons wide, and how many neurons deep, a specified feature map is). Length and width, as used in reference to a feature map, correspond to the spatial dimensions of the image being processed, and may in some cases correspond to a number of pixels/voxels of an image. Depth, as used in reference to a feature map may correspond to a number of features in each feature channel.

The transformations/mappings performed between each feature map are indicated by arrows, wherein each distinct type of arrow corresponds to a distinct type of transformation, as indicated by legend 358. Rightward pointing solid black arrows indicate 3×3 convolutions with a stride of 1, wherein output from a 3×3 grid of features of an immediately preceding feature map (wherein the 3×3 grid extends through all layers of the immediately preceding feature map) are mapped to a single feature, at a single depth, of a current feature map by performing a dot product between the outputs/activations of the 3×3 grid of feature channels and a 3×3 filter, (comprising 9 weights for each layer/unit of depth of the immediately preceding feature map). In some embodiments, the convolutional filter weights may be selected based on output from an acquisition parameter transform. In some embodiments the convolutional filter weights may be learned during a training process. The filters used to perform the 3×3 convolutions are herein referred to as convolution filters, convolutional filters, convolution kernels, or convolutional kernels.

Downward pointing arrows indicate 2×2 max pooling operations, wherein the max value from a 2×2 grid of feature channels at a single depth is propagated from an immediately preceding feature map to a single feature at a single depth of a current feature map, thereby resulting in an output feature map with a 4-fold reduction in spatial resolution as compared to the immediately preceding feature map. In one example, max pooling of a 2×2 grid of activations from an immediately preceding feature map, wherein the 2×2 grid of activations comprises (2, 1.4, 10, 4.4) produces an output of (10), as 10 is the maximum value of the activations within the 2×2 grid.

Upward pointing arrows indicate 2×2 up-convolutions of stride 2, which comprise performing a transpose convolution (also referred to herein as a deconvolution) using a deconvolution filter comprising a plurality of weights (filters used to perform transpose convolutions are herein also referred to as deconvolutional filters or deconvolution filters) mapping output from a single feature channel at each feature depth of an immediately preceding feature map to a 2×2 grid of features at a single feature depth in a current feature map, thereby increasing the spatial resolution of the immediately preceding feature map 4-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map, are equal, no cropping may be performed.

Rightward pointing arrows with hollow heads indicate a 1×1 convolution with stride 1, in which each feature channel in an immediately preceding feature map is mapped to a single feature channel of a current feature map, or in other words, wherein a 1-to-1 mapping of feature channels between an immediately preceding feature map and a current feature map occurs. Processing at every feature map may include the above-described convolutions and deconvolutions, as well as activations, where activation functions are non-linear functions that restrict the output values of the processing to a bounded range.

In addition to the operations indicated by the arrows within legend 358, CNN architecture 300 includes solid filled rectangles corresponding to feature maps, wherein feature maps comprise a height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a left-right length as shown in FIG. 3, corresponds to the number of features within each feature channel). Likewise, CNN architecture 300 includes hollow (unfilled) rectangles, corresponding to copied and cropped feature maps, wherein copied feature maps comprise height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a length from a left side to a right side as shown in FIG. 3, corresponds to the number of features within each feature channel).

Starting at input image tile 302c (herein also referred to as an input layer), data corresponding to a corrupted medical image 302a is input and mapped to a first set of features. In some embodiments, corrupted medical image 302a, which may comprise one or more layers corresponding to one or more features of the image (such as each intensity value of a multi-color image). In some embodiments, labeled images 302b provided as input with the corrupted medical images 302a may indicate an expected position of the interventional device within the corrupted medical images 302a. Corrupted medical images 302a may comprise two-dimensional (2D) or three-dimensional (3D) images/maps of a patient anatomical region. In some embodiments, the input data from corrupted medical images 302a is pre-processed (e.g., normalized) before being processed by the neural network.

Output layer 356a may comprise an output layer of neurons, wherein each neuron may correspond to a pixel of a predicted segmentation medical image 356b (or residual), wherein output of each neuron may correspond to the predicted pixel intensity in specified location within the output segmentation medical image 356b.

In this way, CNN architecture 300 may enable mapping of a plurality of intensity values from a corrupted medical image 302a to a plurality of intensity values of a segmentation medical image 356b, wherein the segmentation medical image 356b depicts the interventional device present within the corrupted medical image 302a. CNN architecture 300 illustrates the feature map transformations which occur as an input image tile is propagated through the neuron layers of a convolutional neural network, to produce a segmented medical image. In one example, CNN architecture 400 may enable mapping of a plurality of pixel/voxel intensity values of a corrupted medical image to a residual map, wherein a segmentation medical image may be produced by combining the residual map with the input corrupted medical image 302a, such as by pixelwise addition of values.

The weights (and biases) of the convolutional layers in CNN architecture 300 may be learned during training. CNN architecture 300 may be trained by calculating a difference between a predicted segmentation medical image, and a ground truth segmentation medical image, wherein the ground truth segmentation medical image may comprise a segmented medical image of an interventional device. The difference between the predicted segmentation medical image and the ground truth segmentation medical image may be used to determine a loss, and the loss may be back propagated through the neural network to update the weights (and biases) of each feature map using gradient descent, or any other method of parameter optimization known in the art of machine learning. A plurality of training data pairs, comprising corrupted medical images and corresponding ground truth segmentation medical images, may be used during the training process of CNN architecture 300.

In one example, dice loss may be used as the loss function for training the CNN architecture 300, such that a dice similarity coefficient (DSC) may be used to generate training loss. DSC comprises a statistic used for comparing the similarity of two sets, and may be calculated according to:

$$DSC(GS, SEG) = \frac{2|GS \cap SEG|}{|GS| + |SEG|},$$

where GS represents the gold standard segmentation of a target region, SEG represents corresponding automatic segmentation, |GS∩SEG| refers to the overlap region, and the |■| operator represents the sum of the entries of the matrix. The dice loss is defined as:

$$LDice=1-DSC.$$

Although not shown in FIG. 3, it will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration.

It should be understood that CNN architecture 300 shown in FIG. 3 is for illustration, not for limitation. Any appropriate neural network can be used herein for predicting a segmentation medical image from a corrupted medical image, such as ResNet, recurrent neural networks, General Regression Neural Network (GRNN), etc. One or more specific embodiments of the present disclosure are described above in order to provide a thorough understanding. These described embodiments are only examples of systems and methods for predicting segmentation medical images from corrupted medical images using a deep neural network. The skilled artisan will understand that specific details described in the embodiments can be modified when being placed into practice without deviating the spirit of the present disclosure.

FIG. 4 shows an example architecture of a generative adversarial network (GAN) 400 configured to restore corrupted ultrasound images to an image quality of reference ultrasound images. In particular, the GAN 400 restores a corrupted ultrasound image 404, or an acquired ultrasound image of an anatomical region wherein the acquired ultrasound image is corrupted with one or more image artifacts caused by an interventional device in the image, to an image quality of a reference ultrasound image 402 of the same anatomical region acquired without the interventional device in the image, such that the GAN 400 outputs a restored image 450 corresponding to the corrupted image without the one or more image artifacts. The GAN 400 may be implemented as the restoration module 216 of the image processing system 202, as an illustrative example.

The GAN 400 comprises a generator 420 and a discriminator 430. The generator 420 and the discriminator 430 comprise deep neural networks configured to generate image data and discriminate image data, respectively. That is, the generator 420 comprises a neural network configured to accept one or more corrupted ultrasound images 404 as input and output generated samples 422. In some examples, the GAN 400 may add additional noise 406 to the corrupted images 404 prior to inputting the corrupted images 404 to the generator 420.

Meanwhile, the discriminator 430 comprises a neural network configured to classify whether an input image is "true" or "false" or more specifically, the discriminator 430 outputs a probability ranging from 0 to 1 of whether the input image is authentic, with 1 representing a prediction of authenticity and 0 representing a prediction of inauthenticity. The reference images 402 are input to the discriminator 430 as a ground truth dataset such that the discriminator 430 learns or trains on the reference images 402, for example via feedback 442.

The generated samples 422 output by the generator 420 are alternatingly input 428 alongside the reference images 402 to the discriminator 430 so that the discriminator 430 may evaluate the generated samples 422.

In other words, the objective of the generator 420 is to learn the distribution $p_\theta(x)$, approximate to the real distribution $p_r(x)$ of the reference images 402, and generate samples 422 that result in a probability distribution $p_G(x)$ equal to the probability density function of the real samples $p_r(x)$. In some examples, the generator 420 may therefore directly learn the differential function $p_\theta(x)$ such that $p_\theta(x) > 0$ and $$\int p_\theta(x)dx = 1,$$

and optimize through maximum likelihood. In other examples, the generator 420 learns the differential transformation function $q_\theta(z)$ of $p_\theta(x)$ and optimizes through maximum likelihood when z is an existing common distribution such as uniform or Gaussian distribution.

Further, the objective of the discriminator 430 is to recognize the data from the real data distribution $p_r(x)$ of the reference images 402, where $D(x)$ indicates the estimated probability of data points $x_i$ in the set $R^n$. In the case of binary classification, if the estimated probability $$D(x_i): \to R^n[0,1]$$

is the positive class $p_i$ and $$1 - D(x_i): \to R[0,1]$$

is the negative class $q_i$, the cross entropy distribution between $p_i$ and $q_i$ is $$L(p,q) = -\Sigma_i^n p_i \log q_i.$$

For a given point $x_i$ and corresponding label $y_i$, the data distribution $x_i$ can be from the real data $x_i \sim p_r(x)$ or the generator data $x_i \sim p_g(z)$.

Considering exactly half of data from the two sources such as real and fake, the generator 420 and the discriminator 430 tend to "fight" each other in a minmax "game" to minimize the loss function. The loss function may thus be given by:

$$\min_G \max_D L((x_i, y_i)_{i=1}^n, D) =$$
$$-\frac{1}{2}E_{x \sim p_r(x)} \log D(x) - \frac{1}{2}E_{z \sim p_r(z)} \log[1 - D(G(z))] + \lambda\Psi,$$

and $$\min_G \max_D L(G, D) =$$
$$-\frac{1}{2}E_{x \sim p_r(x)} \log D(x) - \frac{1}{2}E_{z \sim p_r(z)} \log[1 - D(G(z))] + \lambda\Psi,$$

wherein the term $$\lambda\Psi = E_{x \sim p_r(x)}[(\|\nabla_x\|^2 - 1)^2],$$

is included to overcome the gradient vanish effect.

Thus, by optimizing the generator 420 and the discriminator 430 based on the feedback 442 according to the loss function provided above, the generator 420 accordingly generates a generated sample 422 sufficiently similar to the reference images 402 that the discriminator 430 outputs a probability 440 for the generated sample 422 above a probability threshold. The probability threshold may be selected or set such that generated samples 422 with an output probability 440 above the probability threshold are output as the restored images 450. To that end, the probability threshold may comprise 0.9 or 0.95, as illustrative and non-limiting examples.

In this way, the GAN 400 restores the corrupted images to an image quality similar to the image quality of the reference images 402, to obtain the restored images 450. As the reference images 402 are acquired without an interventional device such as a biopsy needle are present in the imaged area, the restored images 450 do not include the image artifacts caused by the interventional device.

Once the segmentation images are obtained via the CNN architecture 300 depicted in FIG. 3 and the restored images are obtained via the GAN 400 depicted in FIG. 4, the segmentation images and the restored images may be combined to generate output images for display to the user. FIG. 5 shows a diagram illustrating an example method 500 for processing corrupted images 502 to generate output images 522. As mentioned hereinabove, corrupted images 502 are acquired via an ultrasound imaging system, such as the ultrasound imaging system 100 of FIG. 1. The corrupted images 502 depict a given anatomical region of a patient, for example, with an interventional device such as a biopsy needle positioned therein.

In some examples, one or more label images 504 may be provided, which correspond to a label of the interventional device within the corrupted images 502. For example, a user of the ultrasound imaging device may select or indicate, via a user input device 232 for example, the position of the interventional device in the corrupted images 502 to generate the label images 504. At 506, the corrupted images 502 and the label images 504 are input to a deep learning model such as the U-Net model described hereinabove with regard to FIG. 3 for segmentation of the corrupted images 502. In particular, segmentation images 508 comprising the segments of the corrupted images 502 corresponding to the interventional device are output by the U-Net model.

Further, prior to positioning the interventional device within the patient, a plurality of reference images 512 of the same anatomical region as the corrupted images 502 are acquired via the ultrasound imaging system 100. As the reference images 512 are acquired without the interventional device within the anatomical region, the image quality of the reference images 512 is higher than the image quality of the corrupted images 502. At 516, the corrupted images 502 and the reference images 512 are input to a GAN model, such as the GAN 400 described hereinabove with regard to FIG. 4, for restoration of the corrupted images 502. In particular, restored images 518 comprising the corrupted images 502 restored to an image quality similar to the reference images 512 are output by the GAN model at 516.

The segmentation images 508 from the U-Net model and the restored images 518 from the GAN model are synthesized at 520 to produce output images 522. For example, the segmentation images 508 may be superimposed or blended onto the restored images 518 such that the interventional device depicted in the segmentation images 508 is added to the restored images 518, thereby creating the output images 522.

Figure 6:
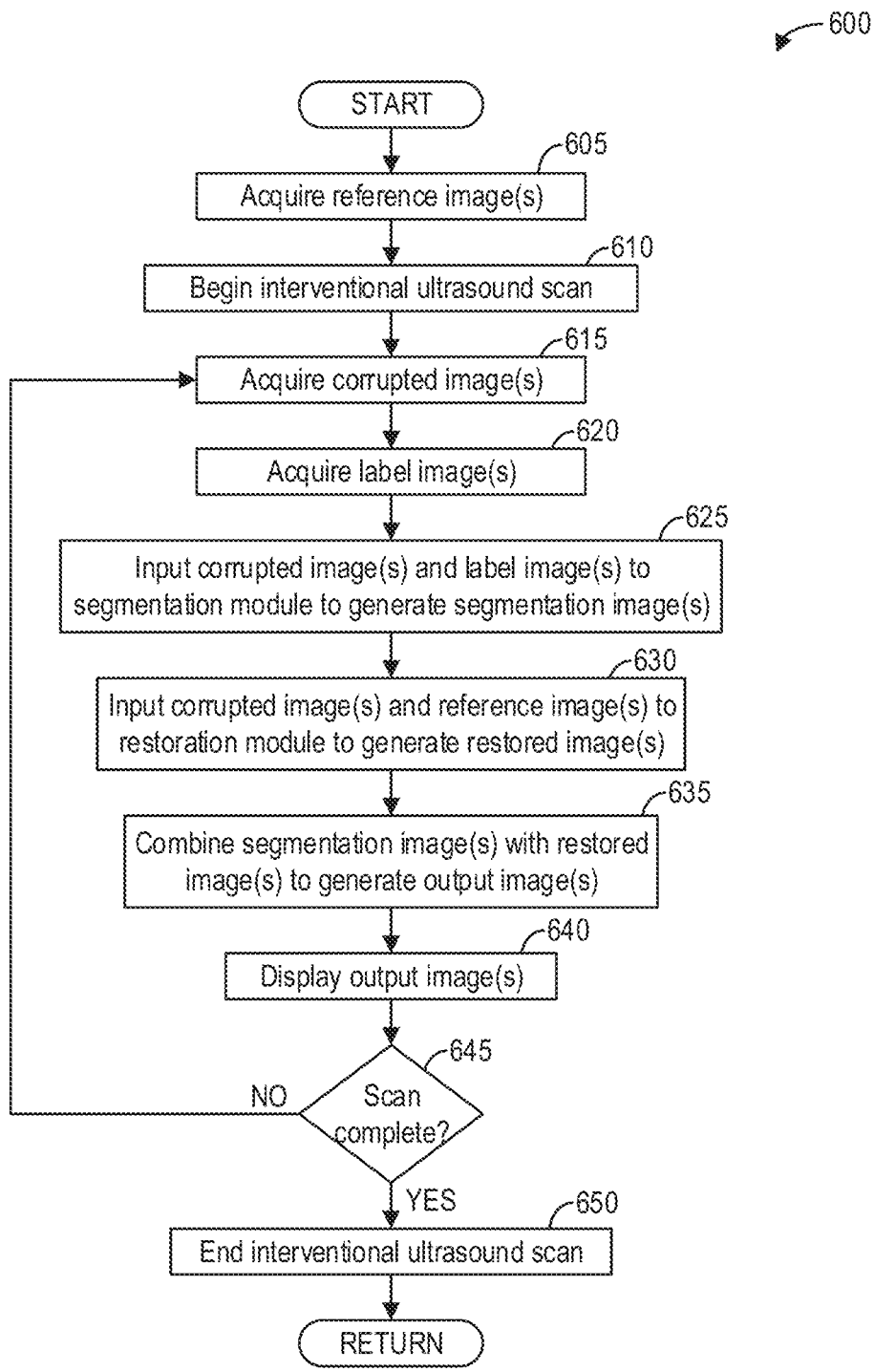
FIG. 6 is a high-level flow chart illustrating an example method for interventional ultrasound imaging, according to an exemplary embodiment.

FIG. 6 shows a high-level flow chart illustrating an example method 600 for interventional ultrasound imaging according to an embodiment. In particular, method 600 relates to processing acquired ultrasound images with multiple deep learning models to improve the image quality of displayed ultrasound images. Method 600 is described with regard to the systems and components of FIGS. 1-4, though it should be appreciated that the method 600 may be implemented with other systems and components without departing from the scope of the present disclosure.

Method 600 begins at 605. At 605, method 600 acquires one or more reference images of an anatomical region of a subject such as a patient, with an ultrasound imaging system such as the ultrasound imaging system 100 of FIG. 1.

After acquiring the reference images at 605, method 600 continues to 610. At 610, method 600 begins an interventional ultrasound scan of the subject. During the interventional ultrasound scan, the ultrasound imaging system images the anatomical region of the subject while a medical operator maneuvers an interventional device, such as a biopsy needle, inserted into the subject in the anatomical region.

During the interventional ultrasound scan, method 600 acquires one or more corrupted images at 615. The corrupted images comprise ultrasound images of the anatomical region of the subject with the interventional device inserted therein. The corrupted images include one or more image artifacts such as reverberation artifacts, comet tail artifacts, side-lobe artifacts, beam-width artifacts, and/or bayonet artifacts caused by the interventional device.

At 620, method 600 acquires one or more label images. As mentioned hereinabove, the label images comprise the corrupted images with the interventional device labeled by the user of the ultrasound imaging system. To that end, to acquire the label image(s), method 600 may display the corrupted image via the display device 234, and receive, via the user input device 232, an indication of the position of the interventional device in the corrupted image. In some examples, method 600 may receive label images initially during the interventional ultrasound scan to assist the deep neural network in segmenting the interventional device in the corrupted images, and method 600 may not further receive such label images after the deep neural network is effectively segmenting the interventional device in the corrupted images. In such examples, the user may opt to provide additional label images if the segmentation is underperforming. In other examples, the user may regularly provide input to create label images throughout the interventional ultrasound scan. In yet other examples, method 600 may not receive label images during the interventional ultrasound scan, and may instead perform the segmentation without label images as input.

Continuing at 625, method 600 inputs the one or more corrupted images acquired at 615 and the one or more label images acquired at 620 to the segmentation module 208 to generate one or more segmentation images comprising the segments of the interventional device. As discussed hereinabove, the segmentation module 208 may comprise a convolution neural network with the CNN architecture 300.

At 630, method 600 inputs the one or more corrupted images acquired at 615 and the one or more reference images acquired at 605 into the restoration module 216 to generate one or more restored images corresponding to the corrupted images with the image quality of the reference images. As discussed hereinabove, the restoration module 216 may comprise a plurality of neural networks configured as the GAN 400.

At 635, method 600 combines the one or more segmentation images generated by the CNN at 625 with the one or more restored images generated by the GAN at 630 to generate one or more output images. In some examples, the segmentation images are superimposed or otherwise blended into the restored images, such that the segmented image of the interventional device is viewed on the restored image. Method 600 then displays the one or more output images, for example via the display device 234, at 640. The output images correspond to the acquired corrupted images of the anatomical region of the subject, however with an image quality similar to the image quality of the reference images acquired at 605. That is, the interventional device is viewable in the output images, while the one or more image artifacts caused by the interventional device viewable in the corrupted images are absent in the output images.

At 645, method 600 determines whether the scan is complete. If the scan is not complete ("NO"), method 600 returns to 615 and continues acquiring corrupted images, processing the corrupted images with the CNN and the GAN, and displaying improved output images. Once the scan is complete ("YES"), method 600 proceeds from 645 to 650. At 650, method 600 ends the interventional ultrasound scan. Method 600 then returns.

Thus, a method for interventional ultrasound imaging comprises acquiring ultrasound images of an anatomical region during an interventional ultrasound imaging scan, the ultrasound images corrupted with one or more image artifacts caused by an interventional device, processing the ultrasound images to generate segmentation images of the interventional device and restored images of the anatomical region without the one or more image artifacts, and displaying output images comprising a combination of the segmentation images of the interventional device and the restored images. As noted above, method 600 is described with regard to a real-time operation such that the output images displayed to the user are useful for accurately guiding the interventional device within the subject. However, it should be appreciated that the method 600 may be applied as a post-processing method after an interventional scan, in instances wherein higher quality ultrasound images of the interventional device within the anatomical region are desired.

A technical effect of the present disclosure includes the display of an ultrasound image of an anatomical region with an interventional device positioned therein with reduced image artifacts. Another technical effect of the present disclosure includes the segmentation of an interventional device within an ultrasound image. Yet another technical effect of the present disclosure includes the restoration of the image quality of a corrupted ultrasound image to the image quality of a reference ultrasound image. Another technical effect of the present disclosure includes the reduction of image artifacts caused by an interventional device in ultrasound images.

In one embodiment, a method comprises acquiring an ultrasound image of an anatomical region, segmenting an interventional device from the ultrasound image to obtain a segmented image, restoring an image quality of the ultrasound image to a reference image quality to obtain a restored ultrasound image, combining the segmented image with the restored ultrasound image to obtain a corrected ultrasound image, and displaying the corrected ultrasound image.

In a first example of the method, the method further comprises acquiring a reference ultrasound image of the anatomical region without the interventional device positioned therein, wherein the reference image quality comprises an image quality of the reference ultrasound image. In a second example of the method optionally including the first example, restoring the image quality of the ultrasound image to the reference image quality comprises inputting the ultrasound image and the reference ultrasound image to a generative adversarial network, wherein the restored ultrasound image comprises an image output by the generative adversarial network. In a third example of the method optionally including one or more of the first and second examples, the image output by the generative adversarial network comprises a sample generated by a generator of the generative adversarial network from the ultrasound image, and wherein the generative adversarial network outputs the image responsive to a discriminator of the generative adversarial network predicting a probability that the sample comprises the reference ultrasound image above a probability threshold. In a fourth example of the method optionally including one or more of the first through third examples, segmenting the interventional device from the ultrasound image comprises inputting the ultrasound image to a convolutional neural network to generate the segmented image. In a fifth example of the method optionally including one or more of the first through fourth examples, the method further comprises inputting a label image indicating a position of the interventional device within the ultrasound image to the convolutional neural network to generate the segmented image. In a sixth example of the method optionally including one or more of the first through fifth examples, the convolutional neural network is configured with a U-Net architecture. In a seventh example of the method optionally including one or more of the first through sixth examples, combining the segmented image with the restored ultrasound image comprises superimposing the segmented image onto the restored ultrasound image. In an eighth example of the method optionally including one or more of the first through seventh examples, the ultrasound image includes one or more image artifacts caused by the interventional device, and the corrected ultrasound image does not include the one or more image artifacts. In a ninth example of the method optionally including one or more of the first through eighth examples, the interventional device comprises a biopsy needle.

In another embodiment, a method comprises acquiring an ultrasound image of an anatomical region with an interventional device positioned therein, processing the ultrasound image with a first deep learning model to obtain a segmented image of the interventional device, processing the ultrasound image with a second deep learning model to obtain a restored ultrasound image of the anatomical region without the interventional device, combining the segmented image with the restored ultrasound image to generate a corrected ultrasound image, and displaying the corrected ultrasound image.

In a first example of the method, the first deep learning model comprises a convolutional neural network. In a second example of the method, the method further comprises acquiring a label image indicating a position of the interventional device within the ultrasound image, and inputting the label image with the ultrasound image to the convolutional neural network to obtain the segmented image. In a third example of the method optionally including one or more of the first and second examples, the second deep learning model comprises a generative adversarial network. In a fourth example of the method optionally including one or more of the first through third examples, the method further comprises acquiring a reference image of the anatomical region without the interventional device positioned therein, and inputting the reference image with the ultrasound image to the generative adversarial network to obtain the restored ultrasound image.

In yet another embodiment, a system comprises an ultrasound probe, a display device, a memory storing instructions, and a processor communicably coupled to the memory and when executing the instructions, configured to: acquire, via the ultrasound probe, an ultrasound image of an anatomical region; segment an interventional device from the ultrasound image to obtain a segmented image; restore an image quality of the ultrasound image to a reference image quality to obtain a restored ultrasound image; combine the segmented image with the restored ultrasound image to obtain a corrected ultrasound image; and display, via the display device, the corrected ultrasound image.

In a first example of the system, the memory stores a convolutional neural network, and when executing the instructions, the processor is configured to input the ultrasound image to the convolutional neural network to segment the interventional device from the ultrasound image. In a second example of the system optionally including the first example, when executing the instructions, the processor is configured to receive a label image indicating a position of the interventional device in the ultrasound image, and input the label image with the ultrasound image to the convolutional neural network. In a third example of the system optionally including one or more of the first and second examples, the memory stores a generative adversarial network, and when executing the instructions, the processor is configured to input the ultrasound image to the generative adversarial network to restore the image quality of the ultrasound image to the reference image quality to obtain the restored ultrasound image. In a fourth example of the system optionally including one or more of the first through third examples, when executing the instructions, the processor is configured to acquire a reference ultrasound image of the anatomical region without the interventional device, and input the reference ultrasound image with the ultrasound image to the generative adversarial network.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method executable by one or more processors executing instructions stored in memory, comprising:
   acquiring an ultrasound image of an anatomical region with an interventional device positioned therein;
   inputting the ultrasound image to a segmentation module to obtain a segmented image of the interventional device;
   entering the ultrasound image and a reference image to a restoration model, the restoration model comprising a generative adversarial network including a generator and a discriminator;

generating a sample with the generator from the ultrasound image, the sample including a version of the ultrasound image without the interventional device positioned therein and with one or more image artifacts caused by the interventional device removed;

predicting, with the discriminator, a probability that the sample comprises the reference image above a probability threshold;

in response to the predicting, outputting the sample as a restored ultrasound image;

combining the segmented image with the restored ultrasound image to obtain a corrected ultrasound image; and displaying the corrected ultrasound image.

2. The method of claim 1, wherein inputting the ultrasound image to the segmentation module comprises inputting the ultrasound image to a convolutional neural network to generate the segmented image, and wherein the segmented image comprises segments of the interventional device in the ultrasound image.

3. The method of claim 2, further comprising inputting a label image indicating a position of the interventional device within the ultrasound image to the convolutional neural network to generate the segmented image.

4. The method of claim 2, wherein the convolutional neural network is configured with a U-Net architecture.

5. The method of claim 1, wherein combining the segmented image with the restored ultrasound image comprises superimposing the segmented image onto the restored ultrasound image.

6. The method of claim 1, wherein the ultrasound image includes one or more image artifacts caused by the interventional device, and wherein the corrected ultrasound image does not include the one or more image artifacts.

7. The method of claim 1, wherein the interventional device comprises a biopsy needle.

8. A method of using a first deep learning model and a second deep learning model to remove image artifacts, comprising:

training, with a computing device, the first deep learning model based on first training data and a first training process to generate a trained segmentation model, the first training data comprising corrupted medical images and corresponding ground truth segmentation medical images, and the first training process including backpropagation and gradient descent using dice loss as a loss function;

training, with the computing device, the second deep learning model based on second training data and a second training process to generate a trained restoration model, the second training data including corrupted images including interventional devices and reference images without interventional devices, the second training process including generating a sample with a generator of the second deep learning model from a corrupted image, generating a probability with a discriminator of the second deep learning model from the sample and a corresponding reference image, and updating the discriminator and the generator based on the probability;

acquiring an ultrasound image of an anatomical region with an interventional device positioned therein;

processing the ultrasound image with the trained segmentation model to obtain a segmented image of the interventional device;

processing the ultrasound image with the trained restoration model to obtain a restored ultrasound image of the anatomical region without the interventional device, the restored ultrasound image comprising a version of the ultrasound image without the interventional device positioned therein and with one or more image artifacts caused by the interventional device removed;

combining the segmented image with the restored ultrasound image to generate a corrected ultrasound image; and displaying the corrected ultrasound image.

9. The method of claim 8, wherein the first deep learning model comprises a convolutional neural network.

10. The method of claim 9, further comprising acquiring a label image indicating a position of the interventional device within the ultrasound image, and inputting the label image with the ultrasound image to the convolutional neural network to obtain the segmented image.

11. The method of claim 8, further comprising acquiring a reference image of the anatomical region without the interventional device positioned therein, and inputting the reference image with the ultrasound image to the generator to obtain the restored ultrasound image.

12. A system, comprising:
an ultrasound probe;
a display device;
a memory storing instructions; and
a processor communicably coupled to the memory and when executing the instructions, configured to:
   acquire, via the ultrasound probe, an ultrasound image of an anatomical region of a patient including an interventional device positioned therein;
   segment the interventional device from the ultrasound image to obtain a segmented image of the interventional device;
   enter the ultrasound image and a reference image of the anatomical region of the patient without the interventional device positioned therein to a restoration model, the restoration model comprising a generative adversarial network includes a generator and a discriminator;
   generate a sample with the generator from the ultrasound image, the sample including a version of the ultrasound image without the interventional device positioned therein and with one or more image artifacts caused by the interventional device removed;
   predict, with the discriminator, a probability that the sample comprises the reference ultrasound image above a probability threshold;
   in response to the predicting, output the sample as a restored ultrasound image;
   combine the segmented image with the restored ultrasound image to obtain a corrected ultrasound image; and
   display, via the display device, the corrected ultrasound image.

13. The system of claim 12, wherein the memory stores a convolutional neural network, and wherein when executing the instructions, the processor is configured to input the ultrasound image to the convolutional neural network to segment the interventional device from the ultrasound image.

14. The system of claim 13, wherein when executing the instructions, the processor is configured to receive a label image indicating a position of the interventional device in the ultrasound image, and input the label image with the ultrasound image to the convolutional neural network, and wherein the restored ultrasound image has a quality that matches a quality of the reference image.

* * * * *